US009931019B2

(12) United States Patent
Herrmann et al.

(10) Patent No.: US 9,931,019 B2
(45) Date of Patent: Apr. 3, 2018

(54) TUBE ASSEMBLY FOR AN ENDOSCOPE (71) Applicant: Ingoscope Systems GmbH

(72) Inventors: Ingo F. Herrmann, Munich (DE);
Bruno Matteja, Mercenasco (IT)

(73) Assignee: Ingoscope Systems GmbH, Berlin (DE)

( * ) Notice: Subject to any disclaimer, the term of this patent is extended or adjusted under 35 U.S.C. 154(b) by 428 days.

(21) Appl. No.: 13/910,365

(22) Filed: Jun. 5, 2013

(65) Prior Publication Data
US 2013/0267780 A1 Oct. 10, 2013

Related U.S. Application Data (63) Continuation of application No. 12/526,967, filed as application No. PCT/EP2008/001238 on Feb. 18, 2008, now Pat. No. 8,469,880.

(30) Foreign Application Priority Data

Feb. 19, 2007 (DE) .......................... 10 2007 008 099

(51) Int. Cl.
*A61B 1/00* (2006.01)
*A61B 1/018* (2006.01)
(Continued)

(52) U.S. Cl.
CPC ........ *A61B 1/00119* (2013.01); *A61B 1/0014* (2013.01); *A61B 1/00121* (2013.01);
(Continued)

(58) Field of Classification Search
CPC ...... A61M 2025/0037; A61M 25/0032; A61M 25/0023; A61M 25/0026; A61M 25/0028; A61M 25/0029; A61M 25/003; A61M 2025/0034–2025/36; A61M 2025/004; A61M 2025/0031; A61B 1/0014;
(Continued)

(56) References Cited

U.S. PATENT DOCUMENTS

| 4,706,656 | A | * | 11/1987 | Kuboto | ............. A61B 1/00135 600/153 |
| 5,199,417 | A | * | 4/1993 | Muller | .................... A61B 1/07 600/128 |

(Continued)

FOREIGN PATENT DOCUMENTS

EP  1 148 988 A2  10/2001
EP  1 477 104 A1  11/2004
(Continued)

*Primary Examiner* — Timothy J Neal
*Assistant Examiner* — Aaron B Fairchild
(74) *Attorney, Agent, or Firm* — Dinsmore & Shohl LLP (57) ABSTRACT The invention relates to a tube assembly for an endoscope comprising a disposable tube that surrounds a working channel and preferably also a flushing channel and fixing means for fixing the disposable tube to the endoscope. Said fixing means have a fixing unit which is used to fix the disposable tube on the distal end of the endoscope in a rotationally and axially fixed manner. The endoscope fixing means also have a guide device which is used to displaceably fix the disposable tube on respective sections of the endoscope that are at a distance from the distal end of said endoscope.

11 Claims, 8 Drawing Sheets

(51) Int. Cl.
*A61B 1/12* (2006.01)
*A61M 25/00* (2006.01)
*F16L 11/12* (2006.01)
*F16L 11/22* (2006.01)
*A61B 1/227* (2006.01)
*A61B 1/233* (2006.01)
*A61B 1/267* (2006.01)

(52) U.S. Cl.
CPC ...... *A61B 1/00128* (2013.01); *A61B 1/00131* (2013.01); *A61B 1/00135* (2013.01); *A61B 1/018* (2013.01); *A61B 1/126* (2013.01); *A61B 1/127* (2013.01); *A61B 1/227* (2013.01); *A61B 1/233* (2013.01); *A61B 1/267* (2013.01); *A61M 25/0023* (2013.01); *F16L 11/122* (2013.01); *F16L 11/22* (2013.01)

(58) Field of Classification Search
CPC . A61B 1/00119; A61B 1/126; A61B 1/00128; A61B 1/012; A61B 1/015; A61B 1/018; F16L 11/00; F16L 11/121; F16L 11/122; F16L 11/22
USPC ........ 600/121–125, 127–129, 153, 130, 114, 600/156–158; 604/40, 43–45; 138/109–11
See application file for complete search history.

(56) References Cited

U.S. PATENT DOCUMENTS

| | | | |
|---|---|---|---|
| 5,483,951 A | 1/1996 | Frassica et al. | |
| 5,702,347 A | 12/1997 | Yabe et al. | |
| 6,071,233 A * | 6/2000 | Ishikawa | A61B 1/0014 600/104 |
| 6,358,200 B1 * | 3/2002 | Grossi | A61B 1/12 600/121 |
| 6,454,702 B1 | 9/2002 | Smith | |
| 6,530,881 B1 | 3/2003 | Ailinger et al. | |
| 6,537,205 B1 * | 3/2003 | Smith | A61B 1/018 600/104 |
| 6,579,582 B1 | 6/2003 | Harhen et al. | |
| 6,733,440 B2 | 5/2004 | Ailinger et al. | |
| 6,740,030 B2 | 5/2004 | Martone et al. | |
| 6,786,884 B1 * | 9/2004 | DeCant, Jr. | A61M 1/3653 604/43 |
| 7,056,284 B2 | 6/2006 | Martone et al. | |
| 2002/0036019 A1 * | 3/2002 | Woelfel | F16L 11/22 138/115 |
| 2003/0040657 A1 | 2/2003 | Yamaya et al. | |
| 2003/0176766 A1 | 9/2003 | Long et al. | |
| 2004/0249246 A1 * | 12/2004 | Campos | A61B 1/0008 600/160 |
| 2005/0234297 A1 * | 10/2005 | Devierre | A61B 1/00087 600/153 |
| 2007/0043324 A1 * | 2/2007 | Shibata | A61M 25/0032 604/192 |
| 2007/0225554 A1 * | 9/2007 | Maseda | A61B 1/018 600/104 |
| 2007/0244353 A1 * | 10/2007 | Larsen | A61B 1/12 600/105 |

FOREIGN PATENT DOCUMENTS

| | | |
|---|---|---|
| WO | 01/49165 A1 | 7/2001 |
| WO | 01/87144 A1 | 11/2001 |
| WO | 02/07787 A2 | 1/2002 |
| WO | 02/13681 A1 | 2/2002 |
| WO | 04/103157 A2 | 12/2004 |
| WO | 05/016181 A2 | 2/2005 |
| WO | 06/033671 A2 | 3/2006 |

* cited by examiner

TUBE ASSEMBLY FOR AN ENDOSCOPE

CROSS-REFERENCE TO RELATED APPLICATIONS

This application is a continuation of U.S. patent application Ser. No. 12/526,967 filed Apr. 26, 2010, which is the U.S. national phase of PCT/EP2008/001238 filed Feb. 18, 2008, which claims priority of German Patent Application DE 10 2007 008 099.0 filed Feb. 19, 2007.

FIELD OF THE INVENTION

The invention relates to the field of endoscopy, in particular to a hose arrangement for fastening to an endoscope.

BACKGROUND OF THE INVENTION

In many sub-areas of medicine, in particular in gastroenterology, endoscopy is a widespread and successful method in the diagnostics and in the treatment of a plurality of diseases. It has proven expedient in this respect to provide imaging endoscopes with hose arrangements which have a passage or a plurality of passages, for example for the guidance of equipment. However, conventional hose arrangements of the aforesaid type frequently prove impractical since the fastening means for the connection of the endoscope to the hose arrangement are frequently designed in a voluminous manner and/or hinder the operation of the endoscope. Furthermore, the arrangement of the passages is frequently designed in a very specialized manner so that a corresponding hose arrangements has to be selected for each application.

SUMMARY OF THE INVENTION

It is therefore the object of the invention to provide a hose arrangement for an endoscope which enables a reliable and space-saving fastening to the endoscope. The fastening of the endoscope should moreover be simple to effect.

This object is satisfied by the features of claim 1.

The hose arrangement in accordance with the invention for an endoscope includes at least one disposable hose which surrounds a working passage. The hose arrangement furthermore includes endoscope fastening means for the fastening of the disposable hose to an endoscope. The endoscope fastening means have a fixing device by which the disposable hose can be rotationally fixedly and axially fixedly attached to the distal end of the endoscope. The endoscope fastening means furthermore have at least one guide device by which the disposable hose can be displaceably fastened to a respective section of the endoscope spaced apart from the distal end of the endoscope.

In other words: the connection between the endoscope and the hose arrangement in accordance with the invention is established by endoscope fastening means which include a fixing device, on the one hand, and a guide device, on the other hand. The fixing device establishes a fixed connection between the endoscope and the hose arrangement, whereby relative movements between the distal end of the endoscope and the hose arrangement are suppressed. It is hereby ensured that an outlet opening of the working passage arranged in the environment of the fixing device always maintains its position relative to the distal end of the endoscope in the use of the endoscope and in particular also on a curvature of the endoscope (e.g. due to an actuation of a Bowden cable). A defined position of a lateral or axial opening of the working passage relative to the distal end of the endoscope is thus ensured, which is important, for example, for the suction of secretions or for a taking of a sample by means of biopsy forceps guided through the working passage, if an observation by means of the endoscope should simultaneously take place.

In contrast, the guide device allows a relative movement between the endoscope and the hose arrangement. This enables compensation movements in the longitudinal direction (longitudinally displaceable fastening) and/or in the peripheral direction of the hose arrangement (rotationally movable fastening) which are necessary due to bends or curvatures occurring during use along the unit of the endoscope and the hose arrangement. Furthermore, the fastening of the endoscope is simplified since a force-transmitting fixation as a rule only takes place at one point of the endoscope—namely at its distal end.

In accordance with an advantageous further development, the disposable hose additionally surrounds at least one flushing passage, with the hose arrangement having an outlet opening of the flushing passage which is arranged offset to distal with respect to the fixing device for the distal end of the endoscope. The hose arrangement furthermore has an opening of the working passage which is likewise arranged offset to distal with respect to the fixing device. It is thus ensured, for example, that an optical system located at the distal end of the endoscope can always be reliably flushed by means of a flushing liquid guided through the flushing passage. The hose arrangement in this case therefore surrounds at least two passages, a working passage and a flushing passage. The outlet opening of the flushing passage and the opening of the working passage are arranged in a section of the hose arrangement which projects beyond the fixing device for the distal end of the endoscope in the distal direction of the hose arrangement, whereby an efficient flushing of an optical system arranged at the distal end of the endoscope is possible by means of a flushing liquid emerging from the outlet opening of the flushing passage. In addition, activities carried out by means of the working passage can be monitored visually by the endoscope.

Advantageous embodiments of the invention are set forth in the dependent claims, in the description and in the drawings.

In accordance with an embodiment of the hose arrangement in accordance with the invention, it includes a single disposable hose at which the working passage and, optionally, the flushing passage are formed.

Alternatively, the disposable hose can also have a reception passage for the reception of an inner hose, with the flushing passage optionally being formed at the disposable hose and the working passage being formed at the inner hose. In this case, the inner hose is longitudinally displaceable and/or rotatable within the reception passage and thus relative to the fixing device for the distal end of the endoscope.

A further alternative embodiment of the hose arrangement includes a disposable hose with a reception passage for the reception of an inner hose, with both the working passage and the flushing passage (where present) being formed at the inner hose. The inner hose is also longitudinally displaceable and/or rotatable within the reception passage and thus relative to the fixing device for the distal end of the endoscope in this variant.

The different variants allow the provision of respective ideal disposable hoses, with the variants including an inner hose having additional degrees of freedom with respect to the positioning of the distal end of the hose arrangement. If the position of the outlet opening of the flushing passage is also of significance for the examination, it can be advantageous that the flushing passage is also made at the at least longitudinally displaceable inner hose. The variant with a single disposable hose in contrast enables the choice of larger cross-sectional surface of the working passage and/or of the flushing passage with a given diameter of the disposable hose and with given minimal hose wall thicknesses.

The hose arrangement can include a closure cap which is fixedly connectable to the distal end of the disposable hose or of the inner hose. The hose arrangement is thus in at least two parts in the axial direction. The closure cap can close at least one axial opening of the disposable hose or of the inner hose. Such a closure cap can be manufactured cost-effectively—for example as an injection molded part of plastic—and enables additional possibilities to adapt the hose arrangement to the respectively present needs.

It is preferred if the closure cap is fixedly connected to the fixing device, is in particular made in one piece with the fixing device. As already explained above, a rotationally fixed and axially fixed connection is present between the fixing device and the endoscope. If the fixing device is now fixedly connected to the closure cap, it is particularly reliably ensured that the closure cap is not lost in endoscopic examinations and/or treatments. In addition, the relative position of the closure cap with respect to the optical system of the endoscope is thereby fixedly defined, which can be advantageous for different examination/treatment methods.

In a further development of the closure cap, the outlet openings of the flushing passage and/or the opening of the working passage are formed at the closure cap.

Provision can be made with advantageous embodiments of the hose arrangement in accordance with the invention with or without closure cap that the opening of the working passage and/or the outlet opening of the optionally present flushing passage are arranged laterally, whereby a flushing of the optical system of the endoscope is, for example, made possible by means of flushing fluid supplied via the flushing passage. The flushing passage is preferably arranged for this purpose, among other things—with respect to a cross-section of the hose arrangement between the working passage and the endoscope fastening means.

The disposable hose or the inner hose can include a closure element which is connectable to the distal end of the disposable hose and which closes at least one of the laterally arranged openings. For example, a hollow-cylindrical—i.e. tubular—closure element can be introduced into the disposable hose or into the inner hose which admittedly does not close the hose in the axial direction, but blocks a lateral outlet opening of the flushing passage and/or a lateral opening of the working passage.

In accordance with an embodiment, the optionally present flushing passage is arranged laterally offset in a cross-section of the hose arrangement—with respect to a connection line between a longitudinal axis of the disposable hose and a longitudinal axis of the endoscope fastening means. The hose arrangement can have two or more flushing passages instead of a single flushing passage. The outlet openings of the flushing passages can be arranged offset to one another in the axial direction of the hose arrangement. A relative offset of the outlet openings in the radial direction or in the peripheral direction can be provided additionally or alternatively. The flushing passages are in particular arranged symmetrically—with respect to the above-named connection line.

In accordance with an embodiment of the hose arrangement in accordance with the invention, the guide device includes a plurality of holding elements which are arranged spaced apart from one another along the length of the disposable hose since a throughgoing guide device, i.e. an uninterrupted guide device, is not necessary in a number of cases. A guide device including a plurality of holding elements additionally allows an easier introduction of the endoscope into the guide device and means low friction forces to be overcome in operation on a relative movement of the endoscope and the disposable hose. Two to three substantially identical holding elements can in particular be provided, for example with an endoscope length of 35 cm. With an endoscope length of 75 cm, three to five holding elements can, for example, be provided; with an endoscope length of 100 cm, for example five to seven holding elements.

It is preferred if the guide device has at least one substantially hollow-cylindrically shaped loop. Such loops are easy to produce or shape, but simultaneously also ensure a reliable guidance of the hose arrangement.

The guide device and/or the fixing device can be made as a fastening element in one piece which surrounds the disposable hose and the endoscope and which has a disposable hose receiver and an endoscope receiver which are defined by a restriction and/or a web which is arranged between the disposable hose receiver and the endoscope receiver.

The fixing device can be designed such that a force-transmitting connection, in particular a friction-locked connection, is established between the disposable hose and the endoscope. An advantageous aspect of the fixing device includes a cuff open at both sides in the axial direction.

In accordance with an embodiment of the hose arrangement, the disposable hose has at least one reinforcement element. The reinforcement element is curvable since it primarily serves for the stabilization of the cross-section of the passages which would, for example, be squeezed together on a pronounced curvature of the disposable hose and less for the stabilization of the longitudinal axis of the hose arrangement although this aspect can also be used in especially configured cases. The stiffness of the cross-section of the reinforcement element and the elasticity with respect to forces perpendicular to the longitudinal axis of the reinforcement element can be selected in accordance with the demands.

The reinforcement element is in particular arranged in a distal region of the hose arrangement which is arranged offset to proximal relative to the outlet opening of the optionally present flushing passage since the most pronounced curvatures are to be expected here with a corresponding actuation of the endoscope. However, additional reinforcement elements can also be provided in further critical regions of the hose arrangement.

The invention also relates to a hose arrangement system which includes a plurality of similar disposable hoses or inner hoses of the explained kind and furthermore at least one closure cap and a closure element of the explained kind, with at least one axial opening of the disposable hose or of the inner hose being closable by connection of the closure cap to one of the disposable hoses or inner hoses, and with at least one laterally arranged opening of the disposable hose or of the inner hose being closable by connection of the closure element to another of the disposable hoses or inner hoses. The working passage of the respective disposable hose or inner hose thus selectively has a lateral or an axial outlet opening.

BRIEF DESCRIPTION OF THE DRAWINGS

The invention will be described in the following purely by way of example with reference to advantageous embodiments and to the drawings. There are shown:

FIG. 4b a perspective view of the closure cap of FIG. 4a;

DETAILED DESCRIPTION OF THE PREFERRED EMBODIMENTS

Figure 1A:
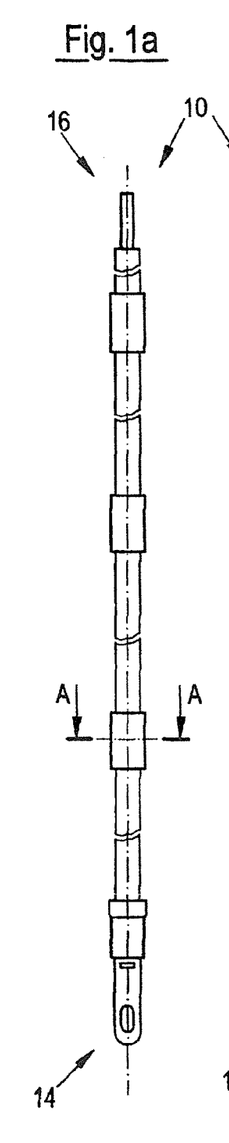
FIG. 1a a schematic representation of an embodiment of the hose arrangement in accordance with the invention.
Figures 1B, 1C, 1D:
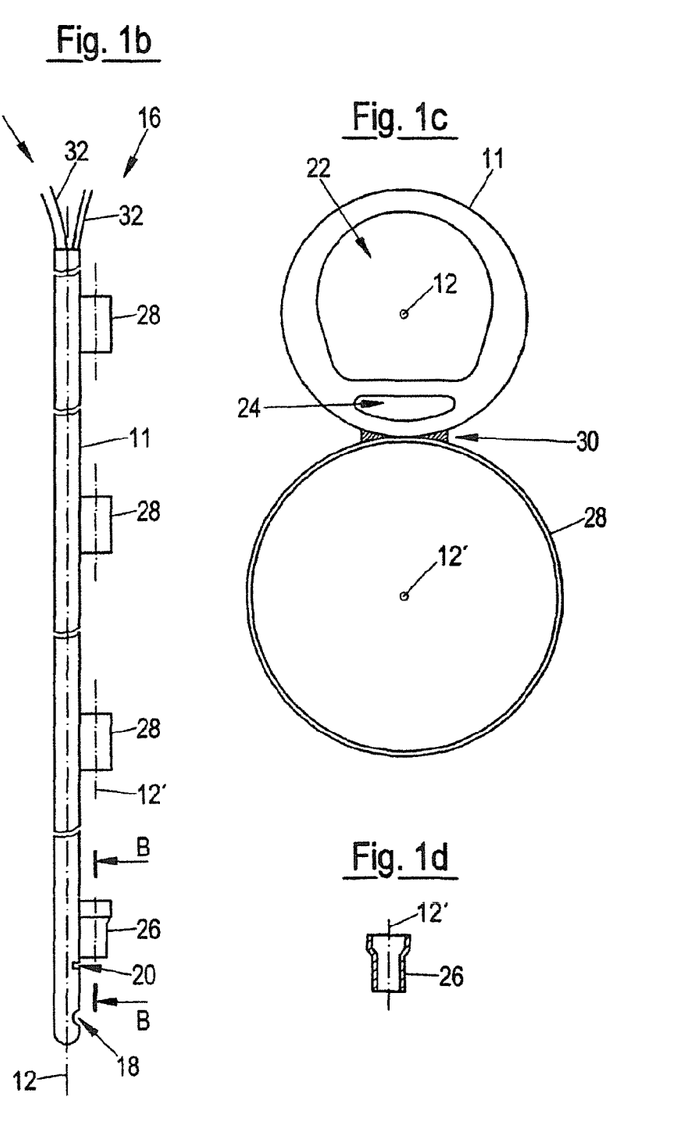
FIG. 1b a view of the hose arrangement of FIG. 1a rotated by 90°.
FIG. 1c a section through the hose arrangement of FIG. 1a along a line AA.
FIG. 1d a section through a fixing cuff of the hose arrangement along the line BB in FIG. 1b.

FIGS. 1a and 1b show a hose arrangement 10 having a flexible disposable hose 11, with FIG. 1b representing a view rotated about a longitudinal axis 12 by 90° with respect to FIG. 1a. The hose arrangement 10 has a distal end 14 and a proximal end 16. In a distal region of the hose arrangement 10 close to the distal end 14, a fixing cuff 26 is fastened to the disposable hose 11. The fixing cuff 26 is arranged further proximal than an opening 18 and an outlet opening 20 so that the distal end of an endoscope (not shown) to be introduced into the fixing cuff 26 is in visual contact with the openings 18, 20 applied to the side at the disposable hose 11—with respect to the longitudinal axis 12. The opening 18 and the outlet opening 20 are in contact with a working passage 22 or an optional flushing passage 24 (shown in FIG. 1c) of the disposable hose 11. As can be seen clearly from FIGS. 1a and 1b, the outlet opening 20 of the flushing passage 24 is arranged offset at a small distance to distal with respect to the fixing cuff 26. Flushing liquid can be sprayed onto the optical system of the endoscope to clean it and, for example, to remove disturbing secretion due to the spatial proximity and the slit-like shape of the outlet opening 20 thus acting as a nozzle. Alternatively to this, air can also be guided through the flushing passage 24 in order to not only blow free the optical system of the endoscope, but also to blow up the hollow space to be examined by air insufflation so that a wall, for example of the stomach or of the esophagus can be observed better.

The opening 18 of the working passage 22 is offset further to distal than the outlet opening 20 relative to the fixing cuff 26. Since it is also arranged on the side facing the fixing cuff 26 with respect to the longitudinal axis 12 of the disposable hose 11, it is, for example, possible to suck off secretion or other substances in the region directly in front of the endoscope.

Guide loops 28 are attached to the disposable hose 11 of the hose arrangement 10 beside the fixing cuff 26. They are arranged at regular intervals, with this only representing a specific embodiment.

FIG. 1c illustrates the design of the hose arrangement with reference to a cross-section along the line AA of FIG. 1a. The cross-section of the disposable hose 11 can be seen in the upper part of FIG. 1c. The disposable hose 11 includes—as already addressed above—the working passage 22 and the optional flushing passage 24. For the better use of the cross-sectional surface of the disposable hose 11, neither the working passage 22 nor the flushing passage 24 are made as circular. in the embodiment of the hose arrangement 10 shown, the working passage 22 has a substantially larger cross-sectional surface than the flushing passage 24. Depending on requirements, a division deviating from this can be selected. The cross-section of the working passage 22 can be described in simplified terms by a combination of a section of an arc of a circle with a part of a trapezoid with rounded corners. The deviation from a circular cross-section of the working passage 22 with a given outer diameter of the disposable hose 11 permits a more efficient passing through of liquid or pieces of fabric. In addition, a piece of equipment with a circular cross-section can be moved more easily in a working passage 22 shaped in this manner since the contact surface to the inner walls of the working passage 22 is smaller than in the case of a circular cross-section and less friction thus occurs.

The side walls of the disposable hose laterally bounding the working passage 22 are in particular made relatively thick, for example, with respect to the wall section of the disposable hose 11 disposed opposite the flushing passage 24. A collapse of the working passage 22 is hereby prevented on a curvature of the disposable hose 11 by means of the endoscope (cf. FIG. 5c).

The cross-sectional shape and size of the flushing passage 24 is optimized such that a sufficient supply of flushing liquid can always be delivered for the cleaning of the optical system of the endoscope with an ideal utilization of the cross-sectional surface of the disposable hose 11. The flushing passage 24 is disposed between the working passage 22 and the guide loops 28, i.e. on a line which connects the longitudinal axis 12 of the disposable hose 11 and a longitudinal axis 12' extending parallel thereto which extends along the longitudinal axes of the guide loops 28 and of the fixing cuff 26.

The lower part of the image in FIG. 1c is taken up by the cross-section of one of the guide loops 28. It has a circular cross-section which serves for the reception of the endoscope. The endoscope can in particular be moved in the longitudinal direction within the guide loop 28. The guide loops 28 thus serve to hold the disposable hose 11 of the hose arrangement 10 in the lateral direction in close spatial proximity to the endoscope, but not to connect them firmly to one another. This is the task of the fixing cuff 26, as already explained above. The guide loop 28 is adhesively bonded to the disposable loop, as indicated by the adhesive connection 30. The type of the connection can, however, be freely selected; for example, a weld connection or a shrink connection is alternatively possible. A one-piece embodiment of the disposable hose 11 and of the guide loops 28 is also conceivable. The same applies accordingly to the fixing cuff 26.

FIG. 1d shows a cross-section through the fixing cuff 26 along the line BB of FIG. 1b. It can be clearly recognized that the inner diameter of the fixing cuff 26 is smaller at distal than at proximal. The fixing cuff 26 preferably comprises an elastic material so that the region of the fixed cuff 26 with a reduced internal radius is widened by the introduction of the distal end of the endoscope 26. A friction-locked connection thereby arises between the fixing cuff 26—which is fixedly connected to the disposal hose 12—and the endoscope. A reliable fixing is thus ensured.

At the proximal end of the disposable hose 11, the working passage 22 and the flushing passage 24 are connected to separate connection hoses 32 which serve for the supply/removal of liquids and/or parts of fabric.

The flushing passage 24 can also be omitted in the embodiment in accordance with FIGS. 1a to 1d, in particular for applications of the hose arrangement 10 in the ear-nose-and-throat field (ENT). In this case, the outlet opening 20 shown in FIGS. 1a and 1b is omitted.

Figure 2A:
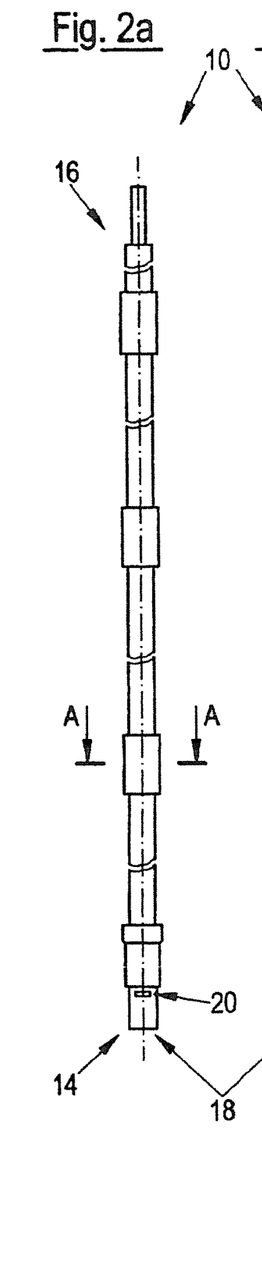
FIG. 2a a schematic representation of a further embodiment of the hose arrangement in accordance with the invention.
Figure 2B:
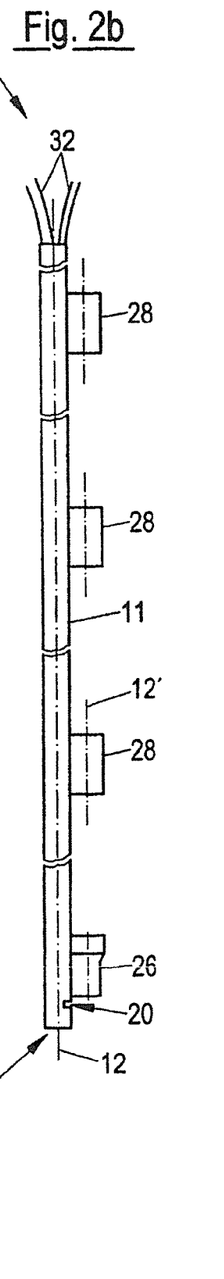
FIG. 2b a view of the hose arrangement of FIG. 2a rotated by 90°.

A somewhat modified embodiment of the hose arrangement 10 is shown in FIGS. 2a and 2b. The two embodiments are similar in many aspects, in particular with respect to the cross-sectional shape of the hose arrangement 10. There is coincidence with respect to the fixing cuff 26 and the outlet opening 20 in this distal region. The opening 18 of the working passage 22 is, however, not attached at the side, but is rather aligned axially with respect to the longitudinal axis 12. In other words, the distal end of the disposable hose 11 is cut-off perpendicular to the longitudinal axis 12. On the one hand, this embodiment can also be used in the present form, for example, for the sucking off of substances. On the other hand, this embodiment is, however, in particular suitable for the guidance of equipment shafts through the working passage 22. This in particular applies when the flushing passage 24 with the outlet opening 20 is omitted. Optionally, the working passage 22 can, however, similar to the embodiment shown in FIGS. 1a and b also be used when an inner hose 34 is used which is guided through the working passage 22.

Figure 2C:
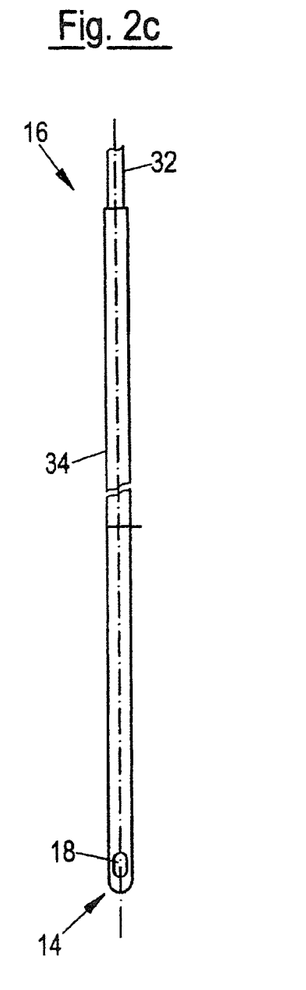
FIG. 2c a schematic representation of an embodiment of an inner hose.

Such an inner hose 34 is shown in FIG. 2c. It is connected to a connection hose 32 at its proximal end 16. The distal end 16 of the inner hose 34 is similar to the tip of the embodiment of the hose arrangement 10 shown in FIGS. 1a and 1b. The inner hose 34 thus has a laterally arranged elongate hole which represents the opening 18. The opening 18 of the inner hose 34 is shown in more detail in FIG. 2d, with the dashed line symbolizing the wall thickness of the inner hose 34. The opening 18 is dimensioned such that it has the largest possible width in a direction perpendicular to the longitudinal axis 12 so that relatively large pieces of tissue or secretion lumps can also be sucked off.

Figure 2D:
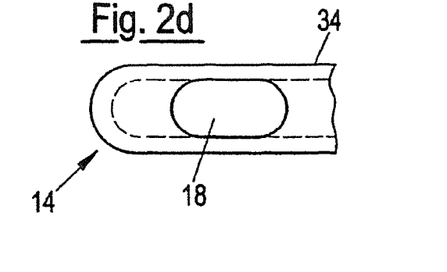
FIG. 2d an enlarged view of the distal end of the inner hose of FIG. 2c.

The advantage of this embodiment in combination with the use of the inner hose 34 lies in the fact that the opening 18 can be positioned by rotating and pushing the inner hose 34 to and fro almost as desired relative to the fixing cuff 26—and thus relative to the endoscope. For example, with an unchanged position of the disposable hose 11 or of the endoscope, a larger region of the examination area can thus be achieved with the opening 18. The treating physician is thus given flexible equipment.

Figure 3A:
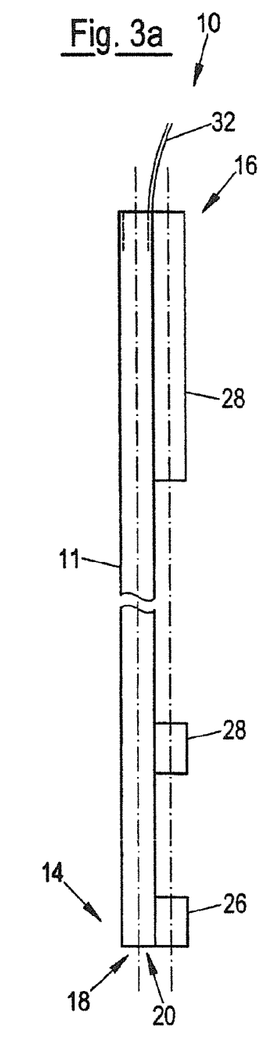
FIG. 3a a schematic representation of a further embodiment of the hose arrangement in accordance with the invention.

A further embodiment of the hose arrangement 10 is shown in FIG. 3a. It shows a disposable hose 11 which is provided with guide loops 28 and a fixing cuff 26. The proximal guide loop 28 has a much larger longitudinal extent than the distal guide loop 28 of the above-treated embodiments. A further difference to the embodiments shown in FIGS. 1a and 1b and 2a and 2b lies in the fact that the distal end of the disposable hose 11 terminates flush with the distal end of the fixing cuff 26. A closure cap 36 (e.g. FIG. 3b) can be introduced into the distal end of the disposable hose 11 which in this case includes a working passage 22 and optionally a flushing passage 24. Embodiments can also be provided in which the closure cap 36 is pushed onto the disposable hose 11 or is otherwise connected to it.

Figures 3B, 3C:
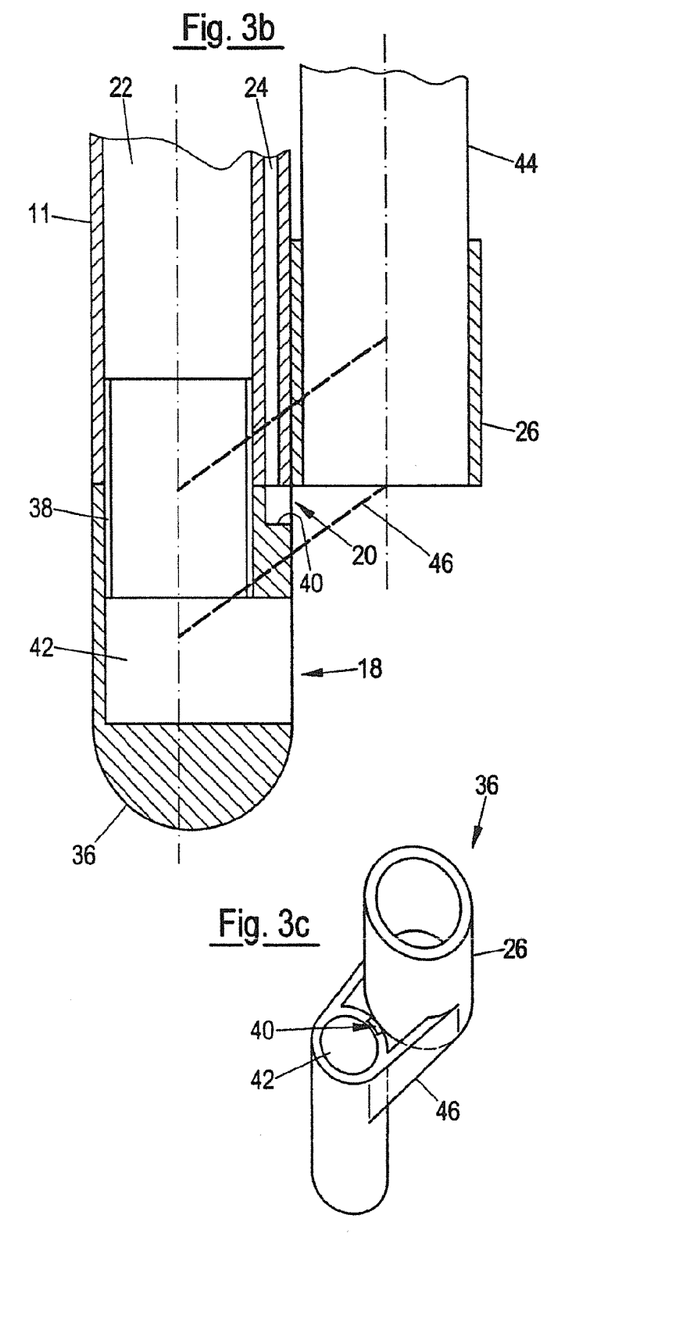
FIG. 3b a schematic sectional view of an embodiment of a closure cap with a fixing device.
FIG. 3c a perspective view of the closure cap of FIG. 3b.

A sectional view through the distal end 14 of the hose arrangement 10 is shown in FIG. 3b. The disposable hose 11 has a working passage 22 and a flushing passage 24. A connection sleeve 38 is plugged into the working passage 22 and is in turn pushed onto the closure cap 36. The connection sleeve 38 and the closure cap 36 can also be made in one piece.

The closure cap 36 has a groove 40. If the closure cap 36 is connected to the disposable hose 11, this groove 40 forms the outlet opening 20 of the flushing passage 24. Furthermore, the closure cap 36 has a passage 42 which is connected to the working passage 22 and which includes a laterally arranged opening 18. Functionally, and with respect to the arrangement of the openings 18, 20 of the passages 22, 24, the embodiment of the hose arrangement 10 shown in FIG. 3b is therefore similar to the embodiment shown in FIGS. 1a and 1b.

The fixing cuff 26, which rotationally fixedly and axially fixedly connects an endoscope 44 to the closure cap 36 and thus to the disposable hose 11 is furthermore an integral component of the closure cap 36.

The detailed representation of the distal end 14 of the hose arrangement 10 illustrates the spatial proximity of the openings 18, 20 to the distal end of the endoscope 44. Flushing liquid can be efficiently sprayed through the outlet opening 20 onto the optical system of the endoscope to clean it. In contrast, secretion or the like can be sucked off simply through the opening 18 in the visual field of the optical system of the endoscope.

The closure cap 36 is a component which is simple to manufacture and which can, for example, has different variations of the shapes and orientations of the openings 18, 20. The openings 18, 20 can also be arranged at different sides. The inner hose 34 can likewise be provided with such a closure cap, both in the embodiment of the inner hose 34 with only one working passage 22 and in the embodiment of the inner hose 34 with a working passage 22 and a flushing passage 24.

A perspective view of such a closure cap is shown in FIG. 3c. The closure cap 36 of FIG. 3c has two connection webs 46 which connects the fixing cuff 26 to the part of the closure cap 36 containing the openings 18, 20. The position of the connection webs 46 relative to the other elements of the closure cap 36 is indicated in FIG. 3b by dashed lines extending obliquely to the longitudinal axes 12, 12'.

The flushing passage 24 with the outlet opening 20 and 40 respectively can also be omitted in the embodiments in accordance with FIGS. 3a to 3c.

Figure 4A:
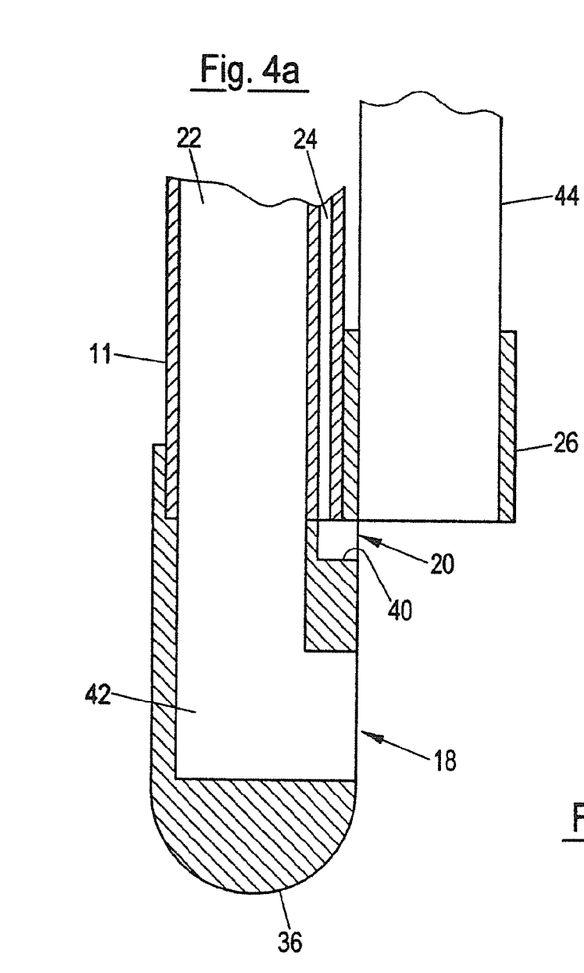
FIG. 4a a schematic sectional view of a further embodiment of a closure cap with a fixing device.

A somewhat different embodiment of a closure cap 36 is illustrated by FIG. 4a. In this embodiment, the closure cap 36 is pushed onto the disposable hose 11 so that a connection sleeve 38 can be omitted. The remaining design of the closure cap 36 is similar to that of the embodiment shown in FIG. 3b.

Figure 4B:
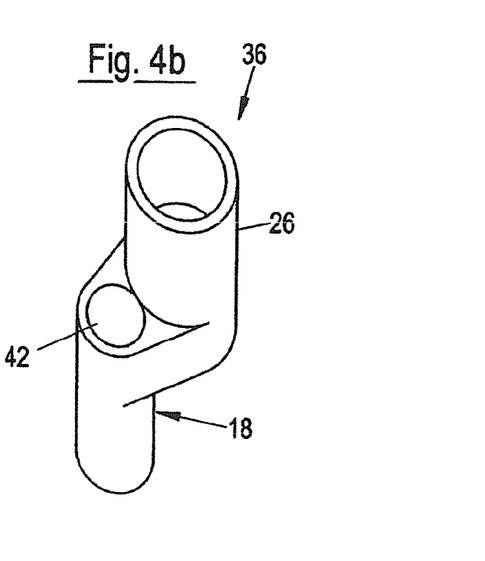

FIG. 4b shows a perspective view of the embodiment of the closure cap 36 shown in FIG. 4a. The groove 40 forming the outlet opening 20 of the flushing passage 24 is in turn arranged at the distal end of the fixing cuff 26 so that the groove 40 cannot be seen in the shown perspective in accordance with FIG. 4b.

Figure 5A:
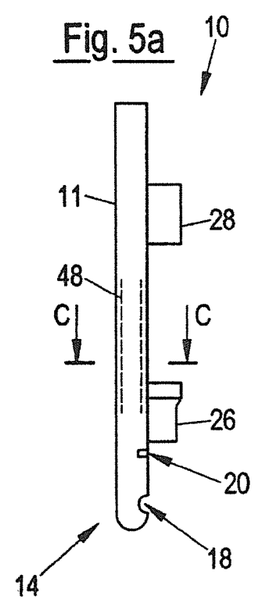
FIG. 5a a schematic representation of an embodiment of the hose arrangement in accordance with the invention with a reinforcement element.
Figure 5B:
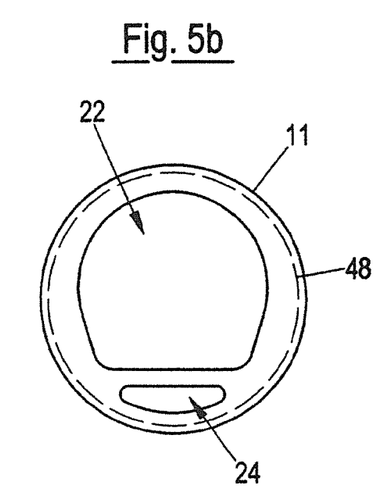
FIG. 5b a section through the hose arrangement of FIG. 5a along a line CC.

An advantageous modification of the hose arrangement 10 is shown in FIG. 5a. The essential features of the distal end 14 of the hose arrangement 10 such as the opening 18, the opening 20 of the optional flushing passage, the fixing cuff 26 and the guide loop 28 have already been described in detail above. The embodiment shown, however, additionally has a spiral spring 48 which is embedded in the disposable hose 11 as can be seen from FIG. 5b. FIG. 5b shows a section perpendicular to the line CC of FIG. 5a.

The spiral spring 48 extends over a section of the distal region of the hose arrangement 10 which is offset to proximal relative to the outlet opening 20 of the flushing passage 24. It is curvable, that is elastically flexible perpendicular to the longitudinal axis 12, with its cross-sectional shape only changing insignificantly on a bending. It is thereby achieved that with a curvature of the hose arrangement 10, the passages 22, 24 are not compressed, whereby, for example, the removal/supply of liquid and/or fabric would be suppressed.

Such a reinforcement element in the form of a spiral spring 48—with other reinforcement elements also being able to be used—is particularly advantageous in situations where the endoscope is brought into inversion. In this state, the endoscope 44 is greatly curved so that the optical system of the endoscope looks "backward" toward proximal (see FIG. 5c). The hose cross-section of the disposable hose 11 would be squeezed together without the spiral spring 48. The supply of, for example, flushing liquid, would thus be interrupted. The same supporting effect can, for example, be achieved by a spiral spring surrounding the disposable hose 11 section-wise.

Figure 5C:
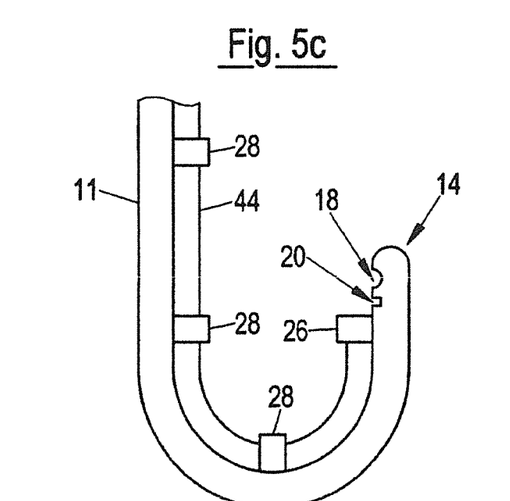
FIG. 5c an endoscope with a hose arrangement in accordance with the invention in a curved arrangement.

It moreover becomes clear with reference to FIG. 5c that the guide loops 28 should permit a relative movement between the endoscope 44 and the disposable hose 11. If the connection between the guide loops 28 and the endoscope 44 were fixed and if no longitudinally displaceable movement were permitted, high stretch loads would arise in the longitudinal direction in the disposable hose 11 or in the endoscope 44 due to the different curvature radii of the disposable hose 11 and of the endoscope 44, which could damage the disposable hose 11, on the one hand, and, on the other hand could also cause a collapse of the cross-sections of the passages 22, 24 or could cause damage to the Bowden cables of the endoscope 44.

Figure 6A:
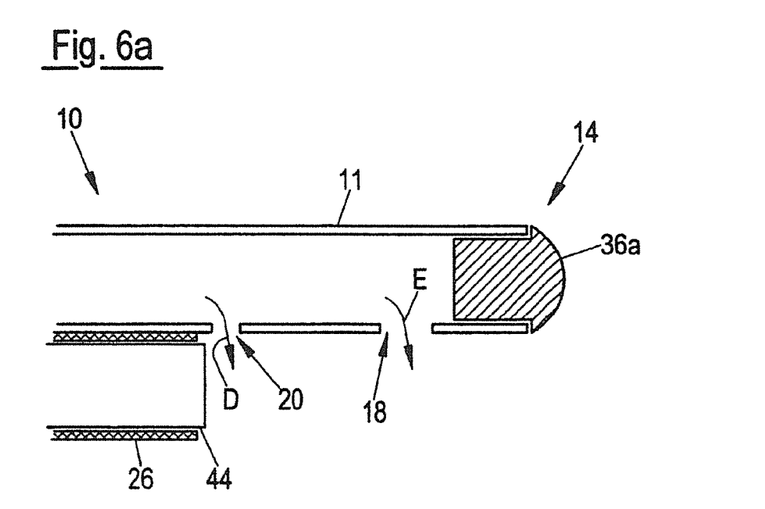
FIGS. 6a and 6b a respective longitudinal section of an embodiment of the hose arrangement in accordance with the invention with a closure piece.

FIG. 6a shows the distal end 14 of an embodiment of the hose arrangement 10. The working passage 22 and the optional flushing passage 24 of the disposable hose 11 are not shown since their arrangement is of subordinate importance for the aspect to be described in the following. The arrows D, E indicate that both the flushing passage 24 and the working passage 22 are connected to a region in front of the endoscope 44 by the lateral openings 20 and 18 of the disposable hose 11. The distal end 14 of the hose arrangement 10 is closed by a closure piece 36a. The two openings 18, 20 offset to one another in the longitudinal direction of the disposable hose 11 are, however, not closed by the closure piece 36a.

Figure 6B:
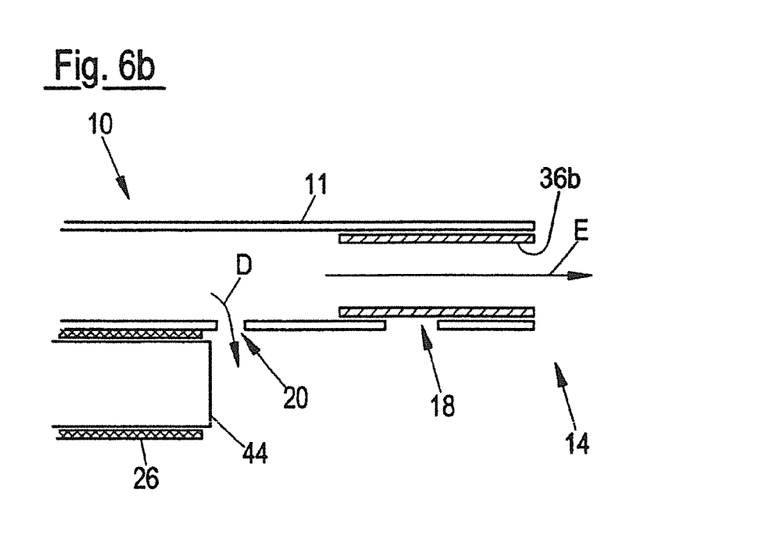

FIG. 6b shows another embodiment of the hose arrangement 10 which, however, makes use of the same disposable hose 11 as the embodiment shown in FIG. 6a. The cap-like or plug-like closure piece 36a of FIG. 6a has here been replaced by a hollow-cylindrical closure piece 36b which leaves the axial opening at the distal end 14 of the disposable hose 11 open. The closure piece 36b closes the lateral working passage opening 18 so that the working passage 22 is now connected to a region in front of the distal end 14 of the hose arrangement 10. The optionally present lateral outlet opening 20 of the flushing passage 24 is still open.

This shows by way of example that different hose arrangement configurations can be realized by the design of the closure piece 36a, 36b without a different embodiment of the disposable hose 11 having to be used. The allows a cost-effective manufacture of the two different configurations (disposable hose 11 as the same part) and also enables the use of endless product for a disposable hose 11 which can be manufactured cost-effectively.

Differing from FIGS. 6a and 6b, the closure pieces 36a, 36b can also be designed so that they are pushed onto the disposable hose 11—not plugged as in FIGS. 6a and 6b—or are fastened thereto in a different manner. Corresponding closure pieces 36a, 36b can also be used in embodiments of the hose arrangement 10 with an inner hose 34.

Figure 7A:
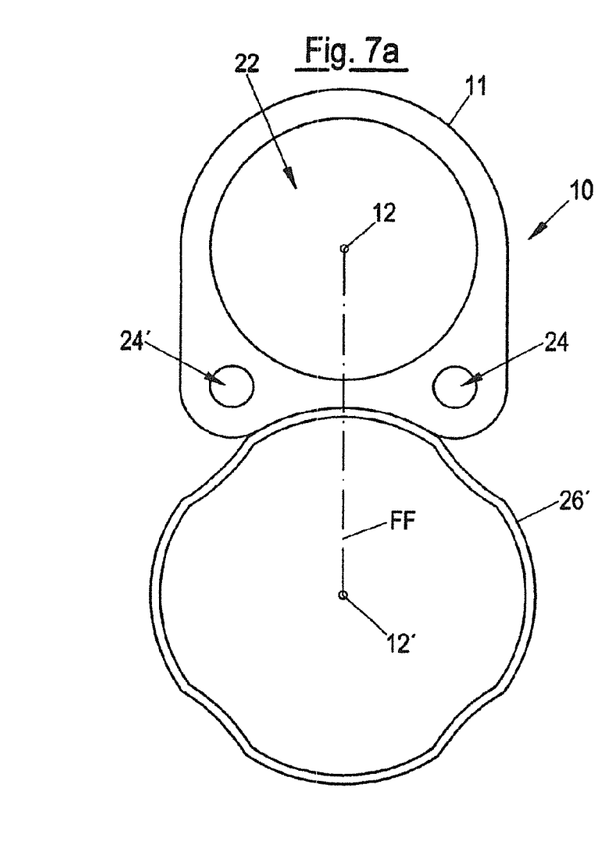
FIGS. 7a and 7b a respective cross-section of an embodiment of the hose arrangement in accordance with the invention with two flushing passages arranged offset and symmetrical or with one flushing passage arranged offset.

The hose arrangement 10 in accordance with the invention can have more than one flushing passage 24, as is shown in FIG. 7a. This embodiment has two flushing passages 24, 24' which are not arranged directly between the working passage 22 and the fixing device—here a fixing cuff 26' with a cross-section sectionally different from a circle. In a cross-section perpendicular to the longitudinal extent of the hose arrangement 10, the flushing passages 24, 24' are offset laterally relative to a connection line FF between the longitudinal axis 12 of the disposable hose 11 and the longitudinal axis 12' of the fixing cuff 26'. They are arranged symmetrically at both sides of the connection line FF.

The offset arrangement of the flushing passages 24, 24' reduces the extent of the hose arrangement 10 in a direction parallel to the connection line FF. In addition, the disposable hose 11 can have a smaller wall thickness in such an aspect for a specific diameter of the working passage 22 (lumen).

The outlet openings 20 of the flushing passages 24, 24' do not have to coincide in the longitudinal direction of the hose arrangement 10 or lie in a common cross-sectional plane, but can rather be arranged as desired to be able to flush different regions—possibly also independently of one another.

Figure 7B:
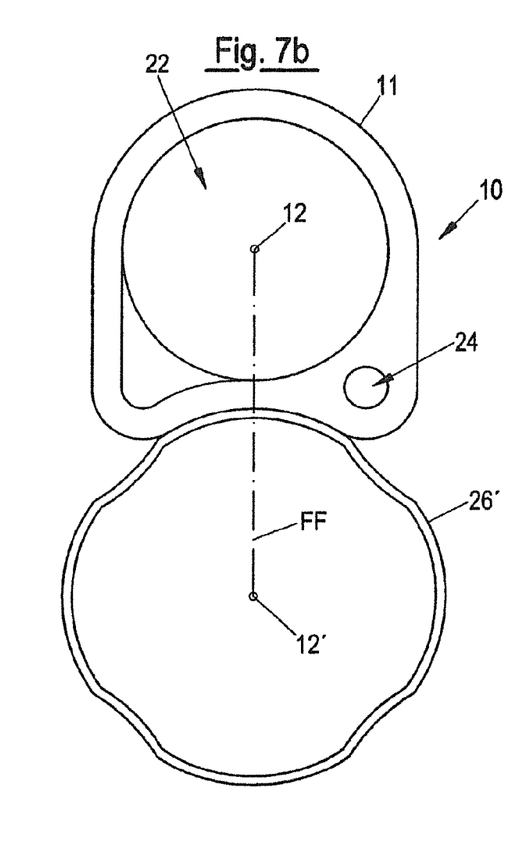

An example for an embodiment having a single offset flushing passage 24 is shown in FIG. 7b. The region of the flushing passages 24' of FIG. 7a was attributed to the working passage. This region can, for example, be utilized for the guidance of a further thin hose or of working means/instruments.

Figure 8A:
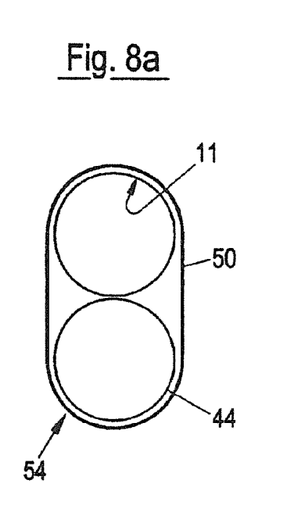
FIGS. 8a to 8c different embodiments of the fixing device and/or of the guide device in a respective cross-sectional view.
Figure 8B:
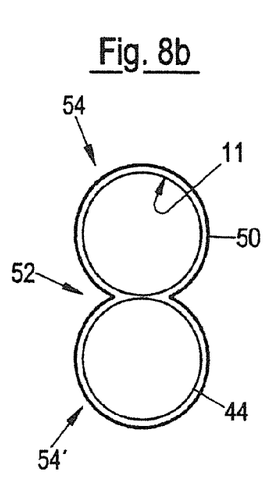
Figure 8C:
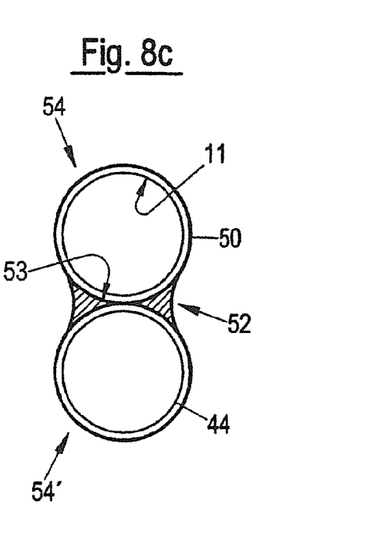

FIGS. 8a to 8c show different embodiments of a fastening element by which the guide loops 28 and/or the fixing cuff 26, 26' can be provided. The fastening element is substantially formed by a one-piece band 50 which is simple to manufacture and which surrounds both the disposable hose 11 and the endoscope 44. The band 50 can be connected releasably or fixedly to the disposable hose 11.

The term "band" is not intended to suggest that the band 50 has to be flexible, for example in the manner of an elastic band. It can in this respect also, for example, be a relatively rigid plastic component.

If the band 50 is acting as a fixing cuff 26, 26', it fixes the endoscope 44 rotationally fixedly and in the axial direction. If it only serves for the guidance of the endoscope 44, it is made such that the endoscope 44 can move relative to the disposable hose 11.

FIG. 8a shows a simple variant of the band 50. It forms a single loop 54 in which the disposable hose 11 and the endoscope 44 are arranged. The loop 54 substantially has the shape of a "0".

In contrast to this, the band 50 of FIG. 8b has a waisting 52 by which two loops 54, 54' are defined so that the band 50 forms a shape similar to an incomplete "8". In other words, the restriction is not complete in the middle region of the band 50, whereby a connection is present between the two loops 54, 54'. The disposable hose 11 is arranged in the loop 54, whereas the loop 54' receives the endoscope 44.

The advantage of the waisted band 50 is that a mutual twisting of the disposable hose 11 and of the endoscope 44 is prevented. Such a twisting in particular creates problems on an inversion of the endoscope 44.

FIG. 8c shows a band 50 with a waisting 52 whose loops 54, 54' are separated from one another by a web 53, whereby the shape of an "8" is formed. The web 50 can also only have the web 53 so that the outer contour of the band 50 corresponds to a "0", as in the case of the embodiment of the band 50 shown in FIG. 5a.

The invention claimed is:

1. A disposable hose apparatus for an endoscope, comprising a disposable hose and fastening means for fastening the disposable hose to an endoscope;
    wherein the disposable hose surrounds a working passage and only a single flushing passage;
    wherein the cross section of said working passage has a substantially flat base section having two side edges, two rectilinear side sections, one of said rectilinear side sections having one side edge connected to and extending outwardly from one side edge of said base section and the other of said rectilinear side sections having one side edge connected to and extending outwardly from the other side edge of said base section, said rectilinear side sections flaring away from each other in a direction away from said base section, and an arc section extending between a second side edge of both said rectilinear side sections;
    wherein the single flushing passage extends adjacent to the base section of the cross-section of the working passage;
    wherein said working passage has a cross-sectional area several times a cross-sectional area of said flushing passage; and
    wherein said fastening means is positioned outside of said disposable hose.

2. A disposable hose apparatus in accordance with claim 1, wherein in the cross-section rounded corners are provided between the base section and the two side sections.

3. A disposable hose apparatus in accordance with claim 1, wherein in the cross-section the base section and the two side sections form three sides of a trapezoid with rounded corners.

4. A disposable hose apparatus in accordance with claim 1, wherein in the cross-section the arc section is formed by an arc of a section of a circle, and wherein the base section is rectilinear.

5. A disposable hose apparatus in accordance with claim 1, wherein the at least one flushing passage is disposed between the working passage and the fastening means.

6. A disposable hose apparatus in accordance with claim 5, wherein said guide loop is circular in shape.

7. A disposable hose apparatus in accordance with claim 5, wherein the fastening means comprise at least one guide loop.

8. A disposable hose apparatus in accordance with claim 1, wherein the at least one flushing passage has a flat cross-section which extends in parallel and adjacent to the base section of the cross-section of the working passage.

9. A disposable hose apparatus in accordance with claim 8, wherein in a cross-section said flushing passage is elongated in a direction parallel to said base section.

10. A disposable hose apparatus in accordance with claim 1, wherein the at least one flushing passage has a flat cross-section comprising an inner section and an outer section, wherein the inner section is rectilinear and extends in parallel and adjacent to the base section of the cross-section of the working passage.

11. A disposable hose apparatus in accordance with claim 1, wherein said hose is a one piece construction.

* * * * *